(12) United States Patent
Rudolph

(10) Patent No.: US 8,136,523 B2
(45) Date of Patent: Mar. 20, 2012

(54) VENTILATION MASK WITH CONTINUOUS SEAL CONNECTED BY RESILIENT CUSHION

(75) Inventor: Kevin A. Rudolph, Overland Park, KS (US)

(73) Assignee: Hans Rudolph, Inc., Shawnee, KS (US)

( * ) Notice: Subject to any disclaimer, the term of this patent is extended or adjusted under 35 U.S.C. 154(b) by 1036 days.

(21) Appl. No.: 12/016,392

(22) Filed: Jan. 18, 2008

(65) Prior Publication Data

US 2008/0230068 A1    Sep. 25, 2008

Related U.S. Application Data

(63) Continuation-in-part of application No. 29/278,067, filed on Mar. 19, 2007, now Pat. No. Des. 573,709.

(51) Int. Cl.
*A62B 18/08* (2006.01)
(52) U.S. Cl. .............................. 128/206.24; 128/206.28
(58) Field of Classification Search ............ 128/205.25, 128/206.21, 206.24, 206.28, 207.11, 207.13
See application file for complete search history.

(56) References Cited

U.S. PATENT DOCUMENTS

| | | | |
|---|---|---|---|
| 2,939,458 A | 6/1960 | Lundquist | |
| 3,343,535 A | 9/1967 | Lytle et al. | |
| 4,315,335 A | 2/1982 | Kennedy et al. | |
| 4,414,973 A | 11/1983 | Matheson et al. | |
| H397 H | 1/1988 | Stark | |
| 4,739,755 A | 4/1988 | White et al. | |
| 4,770,169 A | 9/1988 | Schmoegner et al. | |
| D301,774 S | 6/1989 | Rudolph et al. | |
| 4,907,584 A * | 3/1990 | McGinnis | 128/206.24 |
| D334,633 S | 4/1993 | Rudolph | |
| 5,265,595 A | 11/1993 | Rudolph | |
| 5,349,949 A | 9/1994 | Schegerin | |
| 5,649,532 A | 7/1997 | Griffiths | |
| D385,960 S | 11/1997 | Rudolph | |
| 5,738,094 A | 4/1998 | Hoftman | |
| 6,082,360 A | 7/2000 | Rudolph et al. | |
| 6,192,886 B1 | 2/2001 | Rudolph | |
| D477,074 S | 7/2003 | Rudolph et al. | |
| 6,672,307 B2 | 1/2004 | McDonald et al. | |
| 6,772,760 B2 | 8/2004 | Frater et al. | |
| 6,892,730 B2 | 5/2005 | Griffiths | |
| 6,986,352 B2 | 1/2006 | Frater et al. | |
| 7,523,754 B2 * | 4/2009 | Lithgow et al. | 128/206.24 |
| 2004/0065328 A1 * | 4/2004 | Amarasinghe et al. | 128/206.27 |

* cited by examiner

*Primary Examiner* — Kristen Matter
(74) *Attorney, Agent, or Firm* — Erickson, Kernell, Derusseau & Kleypas, LLC

(57) ABSTRACT

A respiratory mask comprises a sealing flange connected to a mask body by a sinusoidal shaped cushioning member. The cushioning member resiliently compresses when the sealing flange is pressed against the face of a wearer to ensure an airtight seal between the sealing flange and the face of the wearer. The cushioning member functions as a spring, compressing to allow the sealing member to better conform to the face of the wearer but resiliently urging the sealing flange outward against the face of the wearer to prevent leaks.

12 Claims, 7 Drawing Sheets

VENTILATION MASK WITH CONTINUOUS SEAL CONNECTED BY RESILIENT CUSHION

CROSS REFERENCE TO RELATED APPLICATION

This application is a Continuation-in-Part of U.S. Design application Ser. No. 29/278,067 entitled RESPIRATORY MASK, filed Mar. 19, 2007.

BACKGROUND OF THE INVENTION

1. Field of the Invention

The present invention relates to face masks for use in delivering respiratory gasses to a patient under positive pressure including such masks for use in treating sleep apnea or for other conditions requiring non-invasive positive pressure ventilation.

2. Background

The most effective and frequent therapy for obstructive sleep apnea is application of continuous positive airway pressure (CPAP). For such therapy, a patient is fitted with a tight fitting mask connected through an airway to a blower which supplies air to the patient's nasal passages or the nasal passages and mouth at a slight positive pressure. The application of the slight positive pressure is immediately effective in reversing the airway obstructions associated with obstructive sleep apnea. Although the therapeutic results of nasal CPAP are often dramatic and immediate, it is only effective when used properly and on a regular basis. Failure to apply nasal CPAP for even a single night results in recurrence of hypersomnolence the next day resulting from sleep apnea.

Problems associated with wearing existing masks or positive airway pressure delivery systems during periods of attempted sleep are sufficient to deter many patients from continuing CPAP therapy. Some problems include excessive noise and irritation resulting from leaks around improperly fitting masks or general discomfort caused by the design of the mask or the CPAP delivery system. Leakage of air between the mask and the face often allows air to blow on the eyes which wakes the patient and/or substantially irritates the eyes.

Most respiratory masks have integrally formed seals in the form of flexible or pliable flanges, cushions, pillows or the like extending around their outer periphery to form a seal between the mask and the face of the wearer. See for example the masks shown and described in U.S. Pat. Nos. 5,265,595 and 6,192,886. The seals are designed to prevent air from leaking through the interface between the mask and the wearer's face. However, patient movement and variations in the contours of different wearers' faces make it difficult to maintain a complete seal with existing face masks.

There remains a need for a respiratory mask for supplying gas to a patient under pressure which incorporates a seal which readily conforms to varying contours of wearer's to prevent leaks.

SUMMARY OF THE INVENTION

In order to provide a respiratory mask with better sealing capabilities a sealing flange is connected to a mask body by a cushioning member which in a preferred embodiment is S-shaped. The S-shaped cushioning member resiliently compresses when the sealing flange is pressed against the face of a wearer to ensure an airtight seal between the sealing flange and the face of the wearer.

The mask body is generally cup shaped forming a mask chamber or cavity the outer periphery of which is generally circumscribed or defined by a peripheral edge that encircles the nose and mouth of a wearer when the mask body is positioned over the nose and mouth of the wearer. The S-shaped cushioning member includes a first arc which curves inward toward the mask chamber and a second arc which curves outward relative to the first arc and away from the mask chamber to form the s-shape of the S-shaped cushioning member. The S-shaped cushioning member generally functions as a spring, compressing to allow the sealing member to better conform to the face of the wearer but resiliently urging the sealing flange outward against the face of the wearer to prevent leaks.

The sealing flange preferably includes at least an inwardly extending sealing flange and may also include an outwardly extending sealing flange. Positive pressure air delivered into the mask chamber from an inlet in the front of the mask also acts on the inwardly extending sealing flange to urge the flange against the face of the wearer. Resilient ribs are formed in second arc of the S-shaped cushioning member and help resist compression of the second arc. Portions of the ribs also preferably engage the outer surface of the outwardly extending sealing flange to biasingly urge the outwardly extending sealing flange against the face of the wearer.

The mask body, S-shaped cushion, sealing flange assembly and ribs are preferably integrally formed from silicone or other like material that is flexible and resilient and which does not cause substantial skin irritation to the wearer. Rigid plastic supports are mounted on the outer surface of the mask body to provide rigidity to the respiratory mask and to resist excessive outward expansion of the mask body due to the internal pressure exerted on the mask body by the pressurized air directed therein. A first support extends across the portion of the mask extending across the bridge of a wearer's nose. A second support extends across the portion of the mask extending across the wearer's chin. The first and second supports also extend on opposite sides of the mask inlet.

DETAILED DESCRIPTION OF THE PREFERRED EMBODIMENTS

Figure 1:
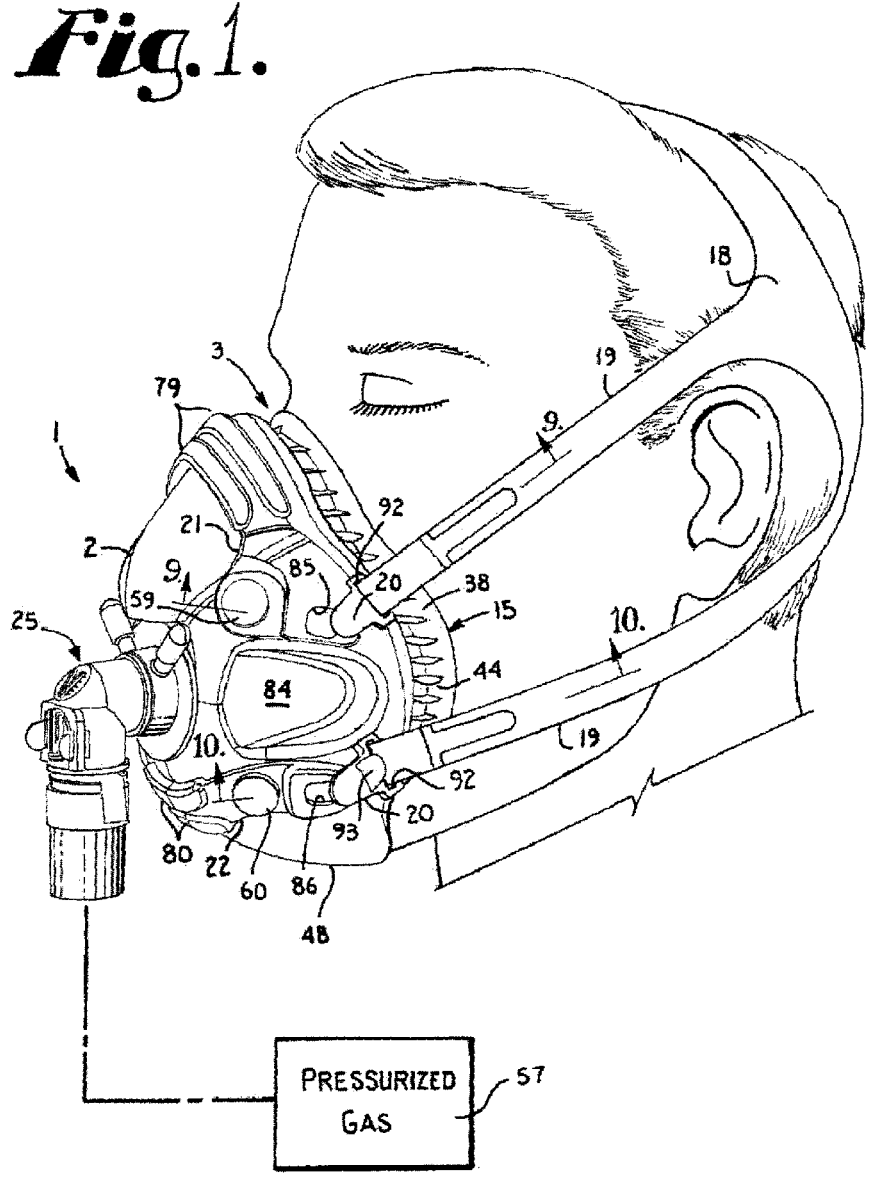
FIG. 1 is a partially schematic, perspective view of a respiratory mask with an improved sealing assembly shown secured to the face of a wearer.
Figure 2:
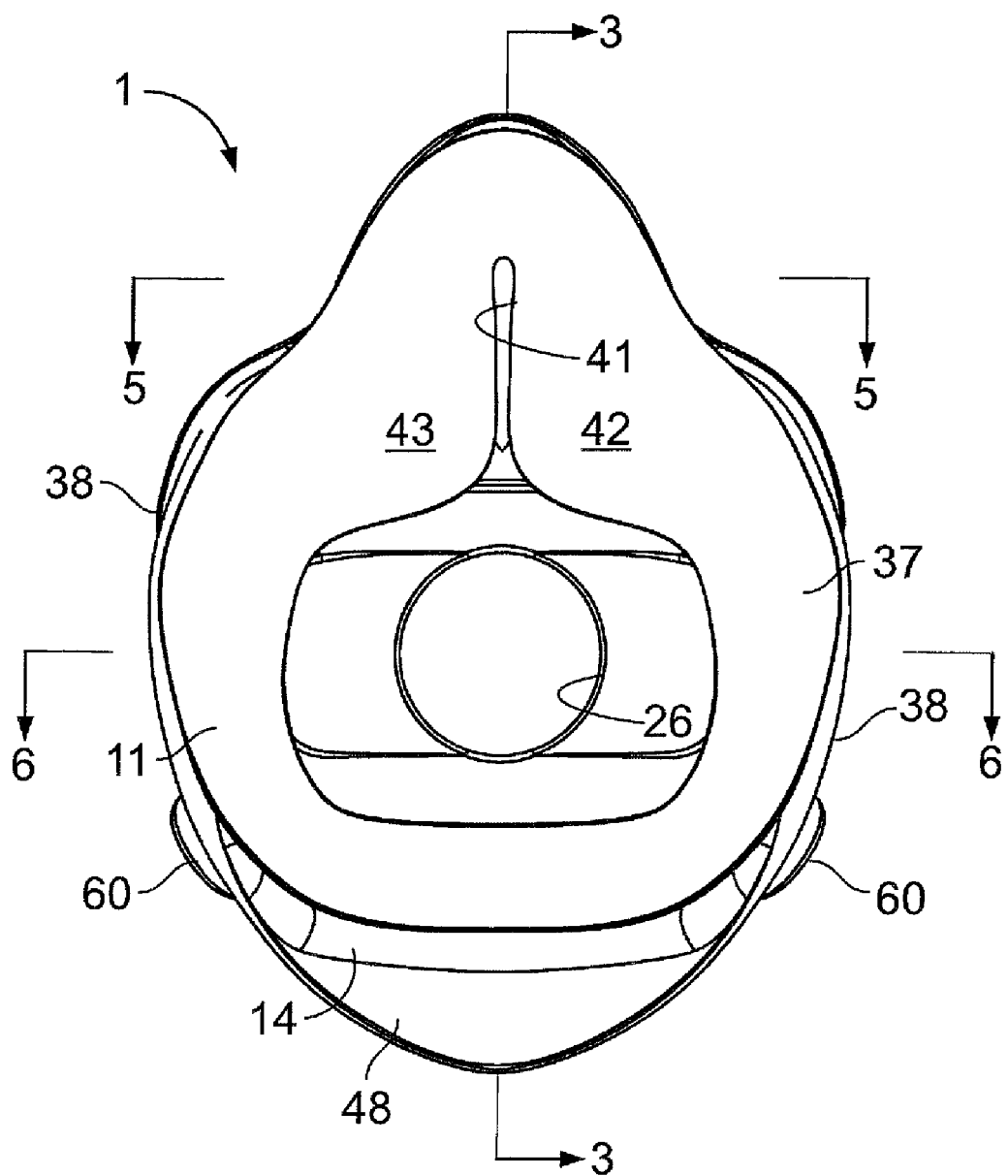
FIG. 2 is a rear view of the respiratory mask.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. The drawings constitute a part of this specification and include exemplary embodiments of the present invention and illustrate various objects and features thereof.

Certain terminology will be used in the following description for convenience in reference only and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

Figure 3:
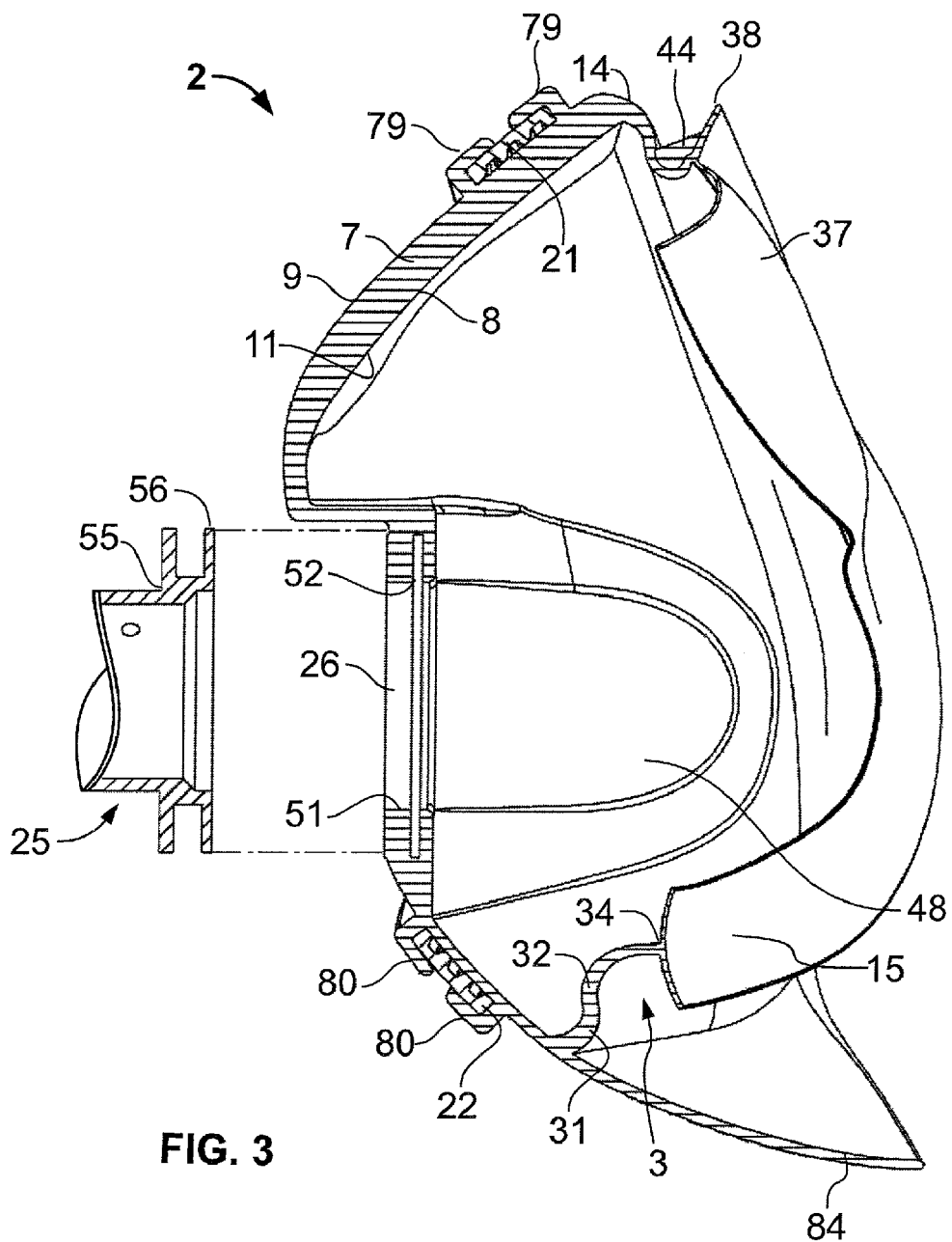
FIG. 3 is an exploded and fragmentary cross-sectional view of the respiratory mask taken along line 3-3 of FIG. 2.
Figure 4:
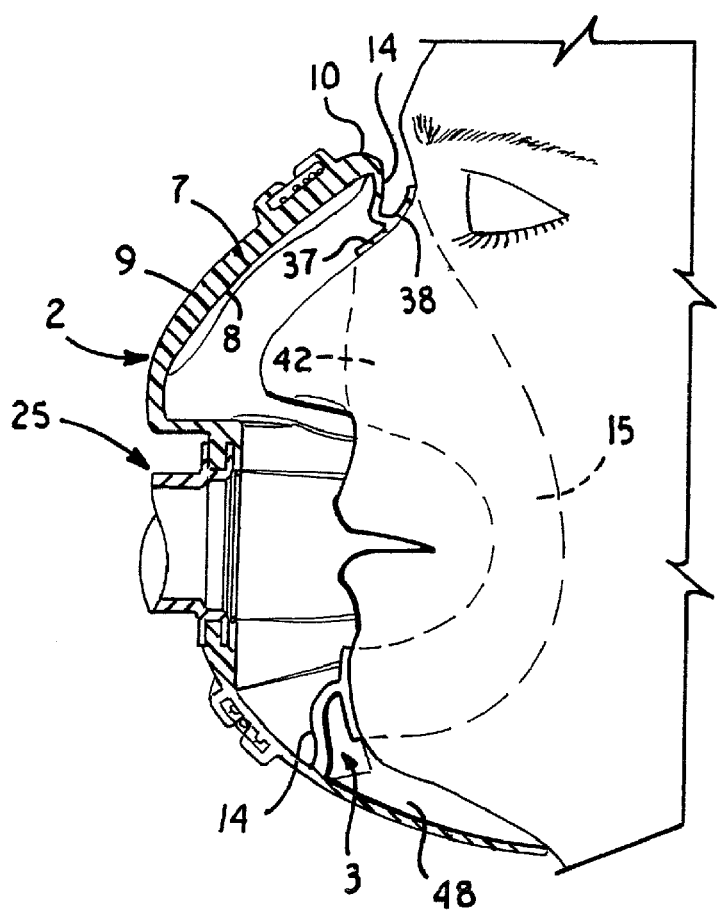
FIG. 4 is a fragmentary cross-sectional view of the respiratory mask similar to FIG. 3 showing the mask, positioned on the face of a wearer.

Referring to the drawings in more detail, the reference number 1 generally designates a respiratory mask with a mask body 2 and an improved seal or sealing assembly 3. The mask body 2 and sealing assembly 3 are preferably constructed of silicone or other rubber-like or elastomeric material that is flexible and yet resilient and that does not cause substantial skin irritation to the user. For example it is foreseen that the mask body 2 and sealing flange assembly 3 could be formed from a thermoplastic elastomer, latex or other rubber-like materials in addition to the preferred silicone rubber. The mask body 2 is generally cup shaped and formed by a wall 7 having an inner surface 8, an outer surface 9 and a peripheral margin, edge or boundary 10. As best seen in FIGS. 3 and 4, the mask body 2 forms an internal chamber or cavity 11 for receiving the nose and mouth of a wearer through the rear open side of the mask body 2. The seal 3 includes a seal cushion or sealing cushion 14 and a sealing flange assembly 15. The seal cushion 14 is connected to and extends from the mask body 2 generally along the peripheral margin or edge 10 of the mask body 2 and the sealing flange assembly 15 is connected to the distal end of the seal cushion 14. The seal cushion 14 may also be referred to as a spring or a spring cushion and is formed from flexible and resilient material to both urge or bias the sealing flange assembly 15 against the wearer's face and to allow the sealing flange assembly 15 to conform to the contours or shape of the wearer's face. The seal cushion 14 is preferably formed in the shape of a compound curve, which includes at least two arc segments to form an s-shape or sinusoidal shape.

The mask 1 is held on a wearer's face by mask securing means, which in the illustrated embodiment comprises a flexible skull cap or harness 18, adjustable securement straps 19 and strap fasteners 20 which connect to rigid braces 21 and 22 which are mounted on the outer surface 9 of the mask body 2. The braces 21 and 22 are relatively rigid and may be formed from a rigid plastic such as a polycarbonate or acrylic plastic. An airflow tubing assembly 25 is connected to the mask body 2 in line with an airflow port or opening 26 formed in the mask body 2 at a position selected to align with the mouth of a wearer of the mask 1. Positive pressure air is generally directed into the mask cavity 11 through the airflow tubing assembly 25 and port 26.

Referring again to FIGS. 3 and 4, the mask body 2 is configured to receive and cover the nose and mouth of a wearer within the internal mask cavity 11. The mask body 2 is sized and configured such that when the mask is positioned against the face of the wearer, the peripheral margin 10 generally extends, across the bridge of the nose, down the sides of the nose, downward across the cheeks of the wearer on opposite sides of the mouth and then underneath the chin of the wearer. The seal cushion 14 is formed on the mask body 2 generally extending from the peripheral margin 10 thereof and continuously around the mask body 2.

The seal cushion 14, with the attached sealing flange assembly 3, extends from the peripheral margin 10 of the mask along the portion adapted to be positioned to extend across the bridge of the nose, down the sides of the nose and downward across the cheeks on either side of the mouth. Instead of following the portion of the peripheral margin 10 adapted to extend under the chin of the wearer, the seal cushion 14, with the attached sealing flange assembly 3, extends across that portion of the inner surface 8 of the mask body 2 that is adapted to be positioned across and in front of the wearer's chin. The sealing cushion 14 is configured and oriented such that the sealing flange assembly 3 is oriented to generally face rearward so that the sealing flange assembly 3 can be pressed rearward against the wearer's face to facilitate formation of a seal between the flange assembly 3 and the wearer's face.

Figure 5:
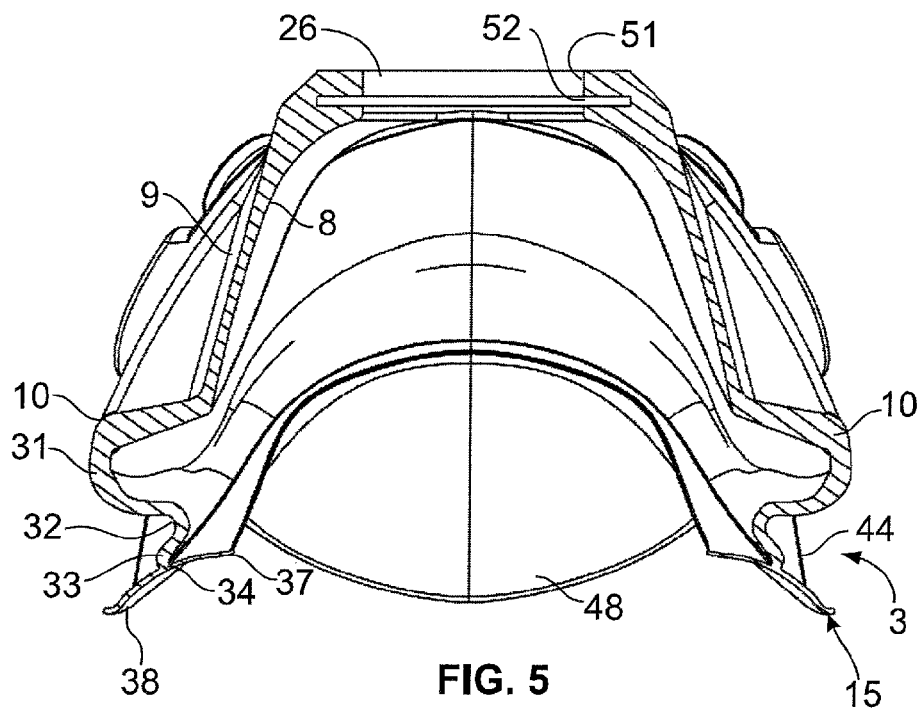
FIG. 5 is a cross-sectional view of the respiratory mask taken along line 5-5 of FIG. 2.
Figure 6:
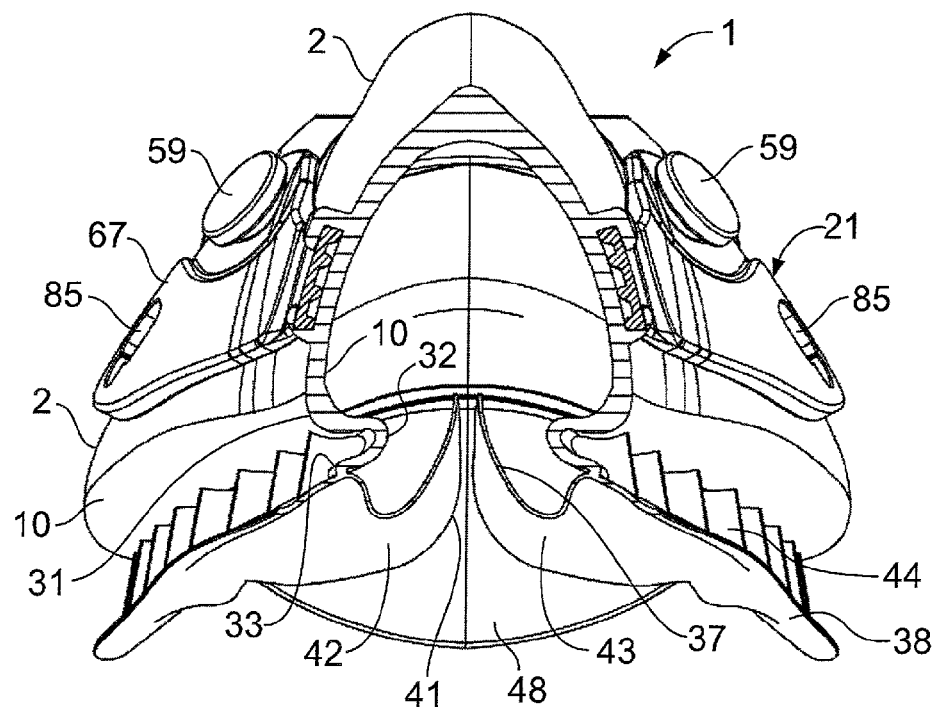
FIG. 6 is a cross-sectional view of the respiratory mask taken along line 6-6 of FIG. 2.

The sealing cushion 14 is preferably formed as a compound curve having at least a first arc or first section 31 that curves inward from the mask body 2 generally toward the center of the cavity 11 formed in the mask body 2, and a second section or second arc 32 that extends from and curves in an opposite direction from the first arc 31 and generally back outward away from the mask cavity 11. As seen in FIGS. 5 and 6, portions of the sealing cushion 14 include a third section or third arc 33, namely all but that portion of the sealing cushion 14 that is adapted to be positioned across the chin of the wearer. The third arc 33 curves in a direction opposite of the curve of the second arc 32. Each of the arcs 31, 32 and 33 is preferably progressively shorter in length and radius. The sealing cushion 14 may also be described as being generally sinusoidal in shape or as forming a sinusoidal spring.

A distal end 34 of the sealing cushion 14, whether at the end of the third arc 33 or the second arc 32, generally faces or projects rearward relative to the front of the mask body 1. The distal end 34 of the sealing cushion 14 is oriented to project toward the face of the wearer against which the mask 1 is to be positioned.

The sealing flange assembly 15 is integrally formed on the distal end 34 of the sealing cushion 14 and preferably includes an inner sealing flange 37 and an outer sealing flange 38. The inner and outer sealing flanges 37 and 38 preferably extend continuously around the mask body 2 along the sealing cushion 14. The inner sealing flange 37 projects inward toward the interior of the mask body 2 or the mask body cavity 11. The outer sealing flange 38 projects outward and away from the interior of the mask body 2. Along the portion of the sealing assembly 3 adapted to be positioned against the cheeks and chin of the mask wearer, both sealing flanges 37 and 38 project generally transverse to the distal end 33 of the sealing cushion 14 and then angle or curve slightly rearward relative to the front of the mask body 2. In a preferred embodiment, the portion of the sealing flanges 37 and 38 adapted to be positioned against the cheeks and chin of the wearer generally present a concave surface, curving toward the face of the wearer.

Along the portion of the sealing assembly 3 adapted to be positioned against the sides of and across the bridge of the wearer's nose, the inner sealing flange 37 initially projects rearward relative to the front of the mask body 2 and then curves around and projects into the internal cavity 11 and toward the front of the mask body 2. The inner sealing flange 37 is sized to be relatively wide along the portion of the sealing assembly 3 intended to extend over the nose with a slit 41 extending between the opposed inner sealing flanges along this portion to receive the wearer's nose. The portions of the inner sealing flange 37 adapted to extend over or against the nose of the wearer may be referred to as nose flaps 42 and 43.

The inner sealing flange 37 is formed relatively thin, with a thickness of approximately 0.018 to 0.20 inches near the inner edge thereof. The thin construction of the inner sealing flange 38 allows it to more readily conform to the unique contours of the specific wearer's face. In addition when pressurized air is pumped into the mask cavity 11, the pressurized air acts against the inner surface of the inner sealing flange 37 to urge the inner sealing flange 37 against the face of the wearer to improve the seal. The large size of the nose flaps 42 and 43 helps ensure a proper seal around the wearer's nose regardless of its size or shape, which can vary significantly.

Elastic ribs 44 are formed on the sealing assembly 3 on the outside of the seal cushion 14 and preferably at least inside the second arc 32 to provide some resistance to compression of the second arc 32 and the sealing cushion 14. For most of the ribs 44, a first end of the rib 44 is connected to the outer surface of the first arc 31 and a second end of the rib is connected to the outer surface of the outer sealing flange 38 to provide resistance to compression of the outer sealing flange 38 relative to the first arc 31 and the mask body 2. In the embodiment shown, elastic ribs 44 extend along the length of the seal cushion 14 except for that portion adapted to be positioned across the chin of the wearer.

The seal cushion 14 gradually tapers or reduces in thickness from the peripheral margin 10 of the mask body to the distal end 34 of the seal cushion 14. The distal end 34 is preferably only half or one third as thick as the peripheral margin 10 of the mask body 2. The mask body 2 generally needs sufficient thickness to prevent excessive distortion of the shape or rupturing of the mask body 2. However, pressing of the relatively thick-walled and rigid peripheral margin 10 of the mask body 2 against a wearer's face would rapidly cause uncomfortable wearing and possibly necrosis of the patient's skin, particularly across the bridge of the wearer's nose.

The seal cushion 14, disclosed herein, generally positions the sealing flange assembly 15 rearward and slightly inward from the peripheral margin 10 of the mask body 2. As the mask 1 is pressed or drawn against a wearer's face, the relatively thin walled seal cushion 14 compresses or gives to conform to the unique contours of the wearer's face. The seal cushion 14 has sufficient resiliency to resist complete compression of the seal cushion 14 to prevent the sealing flange assembly 15 from bottoming out relative to the peripheral margin 10 of the mask body 2. The forces used to draw the mask against the wearer's face are therefore spread out over the larger surface area of the sealing flange assembly 15 and are not focused along the more rigid peripheral margin 10 of the mask body 2, thereby reducing the development of pressure sores or the like.

The portion of the mask body 2 adapted to extend under the chin of a wearer and past the sealing assembly 3 may be referred to as a chin cup 48. Because the chin cup 48 is formed integrally with the mask body 2 and the sealing assembly 3, when a user lowers his or her jaw, extension or stretching of the chin cup 48 simultaneously pulls the sealing assembly 3 positioned across the chin downward with the chin to maintain the proper sealing arrangement.

As discussed above, the airflow opening or port 26 extends through the mask so as to flow communicate with the internal chamber or cavity 11. The opening 26 is generally positioned to be aligned with the mouth of a user when the mask 5 is abuttingly positioned against the face of a user. The opening 26 is further sized so as to generally encircle the opening formed by the mouth of the user when the mouth is used for breathing during ventilatory measurement and analysis procedures. The opening 26 is defined by a grooved circular shoulder 51, extending through the face mask 1 from the inner surface 8 to the outer surface 9. A rim receiving groove 52 extends into the mask body 2 along the grooved circular shoulder 51.

The airflow tubing assembly 25 is connected to the face mask 1 at the circular opening 26 by an annular connecting member 55. The annular connecting member 55 includes a connecting rim 56. The airflow tubing assembly 25 may be of the type including a valve to control the direction of flow of inhalation and exhalation gasses through different openings or passageways. Pressurized air can be supplied to the mask cavity 11 from a source of pressurize air 57 (shown schematically in FIG. 1) through the airflow tubing assembly 25.

Each of the upper and lower rigid braces 21 and 22 is connected to the face mask 1 by first and second pairs of flexible mounting buttons 59 and 60 respectively formed on the outer surface 9 of the mask body 2. The buttons 59 and 60 are integrally formed of the same flexible material as the rest of the mask body 2 and each comprises a cylindrical post 63 and an enlarged cylindrical head 64.

Figure 7:
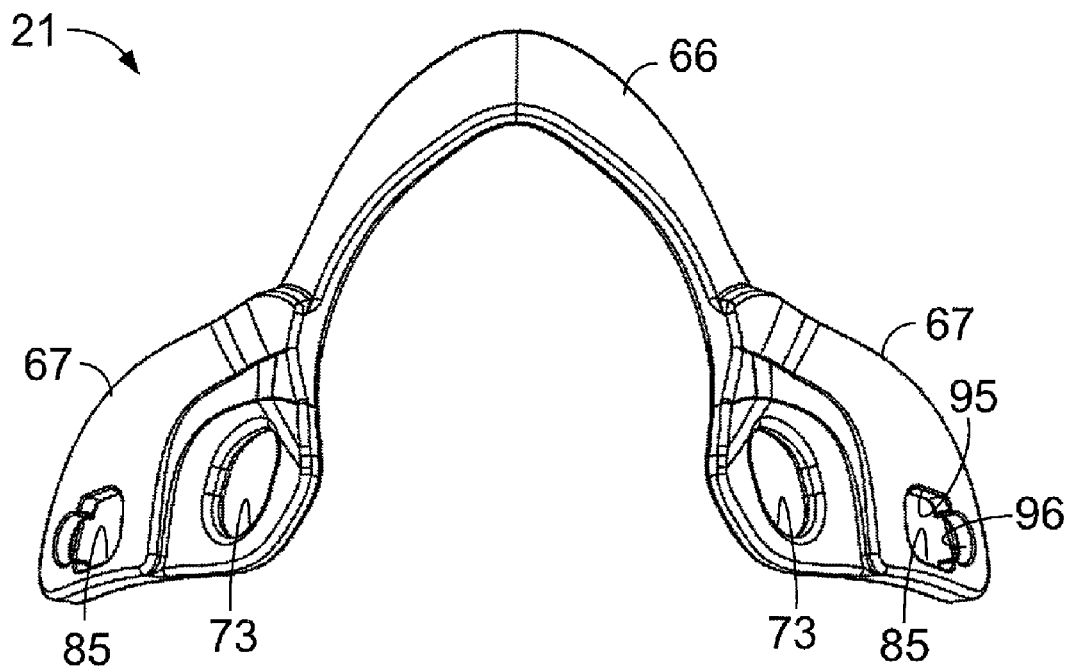
FIG. 7 is an enlarged perspective view of an upper brace of the respiratory mask.
Figure 8:
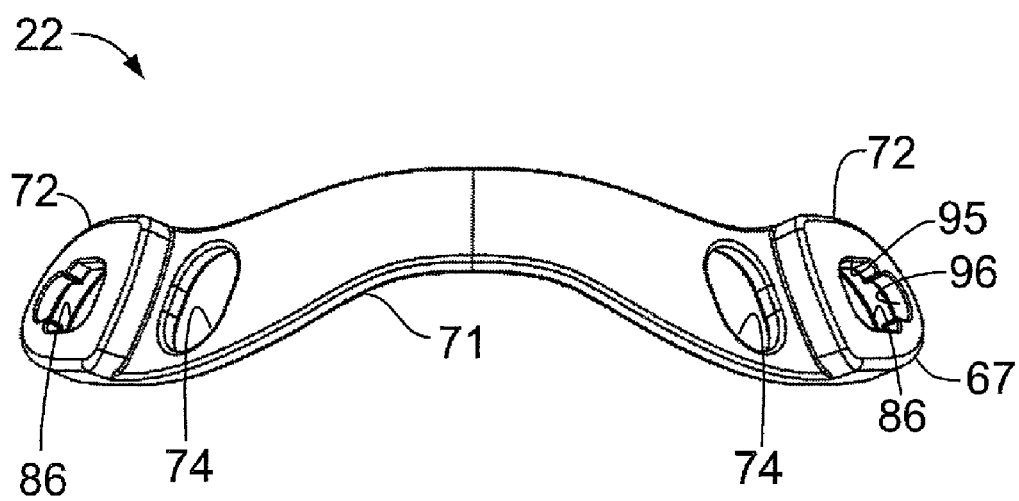
FIG. 8 is an enlarged perspective view of a lower brace of the respiratory mask.
Figure 9:
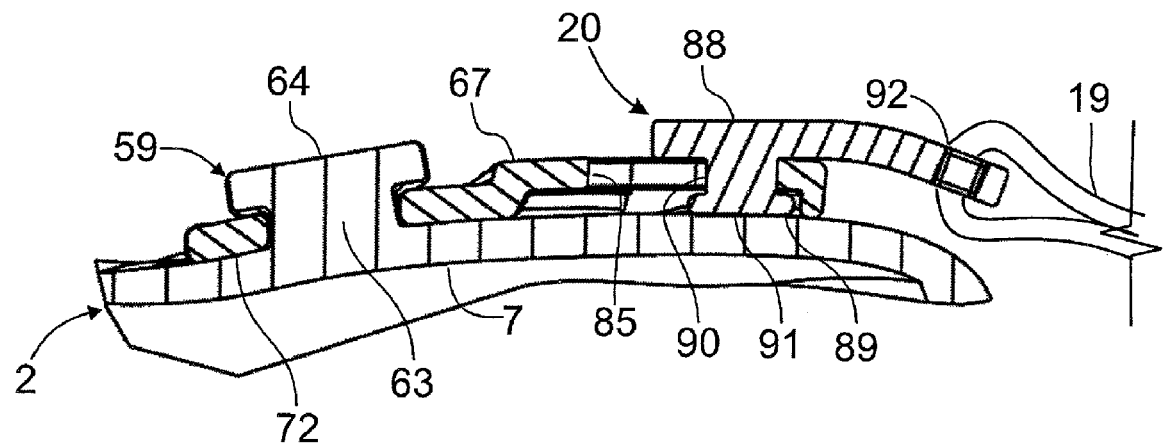
FIG. 9 is an enlarged and fragmentary cross-sectional view taken generally along line 9-9 of FIG. 1.
Figure 10:
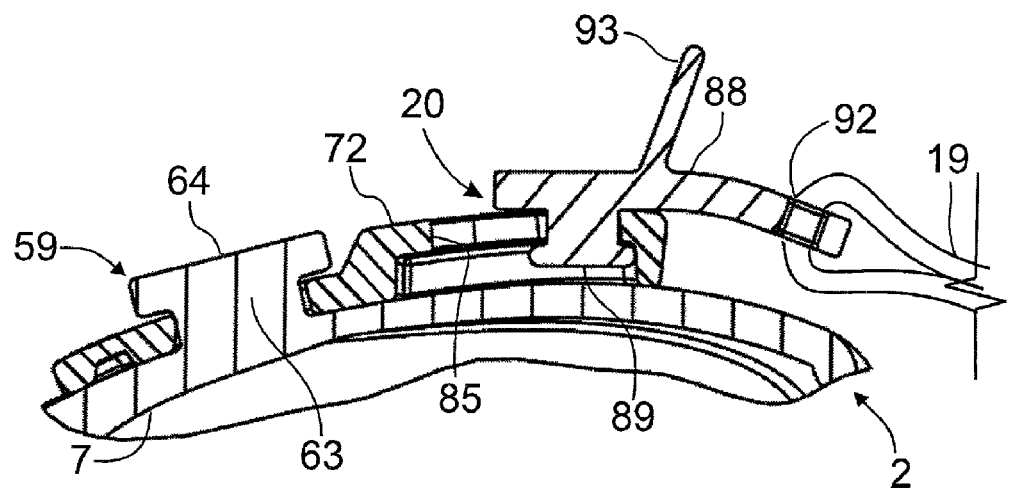
FIG. 10 is an enlarged and fragmentary cross-sectional view taken generally along line 10-10 of FIG. 1.

As best seen in FIGS. 7 and 8, each brace 21 and 22 is generally bowed inward to conform to the side to side contour of the mask body 2. The upper brace 21 includes a relatively narrow central band 66 with enlarged mounting structure 67 formed on each end thereof. Lower brace 22 also includes a central band 71 with mounting structure 72 formed on each end thereof. The central band 66 of the upper brace 21 is positioned to extend across the portion of the mask body 2 covering the bridge of the wearer's nose. The central band 71 of the lower brace 22 is positioned to extend across the portion of the mask body 2 covering the wearer's chin.

A pair of button receiving holes 73 and 74 are formed in the mounting structures 67 and 72 respectively of each rigid brace 21 and 22. Each of the holes 73 and 74 is preferably oblong with one axis longer than the diameter of the button head 64 and a second axis narrower than the button head 64 diameter. The gap between the head of each button 59 and 60 and the outer surface 9 of the mask body 2 is approximately equal to the thickness of the respective braces 21 and 22. The heads 64 of each of the buttons 59 and 60 are pressed through the button receiving holes 73 and 74 to hold the braces 21 and 22 in place against the outer surface 9 of the mask body 2.

First and second pairs of channel forming shoulders 79 and 80 are formed on the outer surface 9 of the mask body 2 above and below the opening 26 respectively. The central portion 66 and 71 of rigid braces 21 and 22 respectively are secured between the first and second pairs of channel forming shoulders 79 and 80 respectively to prevent reduce movement of the braces 21 and 22 relative to the mask body 2.

Recesses or indentations 84 may be formed in the mask body 2 on opposite sides of the airflow opening or port 26. The indentations 84 are preferably sized slightly wider than a wearer's fingers so that the thumb and an opposed finger of the wearer may be positioned in the indentations 84 to facilitate grasping and handling of the mask body 2. The recesses 84 also function to reduce the volume of the internal chamber or cavity 11 in the mask body 2, reducing dead air space and enhancing the performance of the mask for most ventilation purposes.

Receivers 85 and 86 for the strap fasteners 20 are formed in each of the mounting structures of braces 21 and 22 respectively near the distal ends thereof such that at least one strap 19 may be connected to both ends of each brace 21 and 22. Each of the strap fasteners 20 comprises a fastener base 88 with a post 89 having a cylindrical shaft 90 and an enlarged head 91 formed on a distal end thereof projecting outward from one side of the fastener base 88. A slot 92 is formed in the base 88 through which a strap 19 may be threaded and folded over back onto itself and secured together with hook and loop type fasteners or the like for adjustably securing the strap 19 to the fastener 20. A grip 93 may be formed on the fastener body 88 on a side opposite the post 89 to facilitate gripping and manipulation of the fastener 20.

The fastener receivers 85 and 86 shown are generally keyhole type openings with a wide end 95 and a narrow end 96. The wide end 95 is wider than the diameter of the post head 90 and the narrow end 96 is narrower than the diameter of the head 90 and slightly wider than the diameter of the post shaft 90 for receiving and frictionally retaining the shaft 90 therein.

The length of the straps 19 are adjustable to allow the wearer to draw the mask 1 against there face with sufficient force to ensure a proper seal is maintained by the sealing assembly 3. The straps 19 and the cap 18 may be formed from elastic material to accommodate movement of the wearer's face and head. As discussed previously as the mask body 2 is drawn against the face of the wearer, the seal cushion 14 compresses and generally biases the sealing flange assembly 15 against the face of the wearer.

The rigid braces 21 and 22 help resist deformation of the mask body 2 due to the pressures exerted thereon by the pumping of pressurized air into the internal chamber 11 of the mask body 2. By reinforcing the flexible mask body 2 with rigid braces 21 and 22 the thickness of the wall 7 forming the mask body can be reduced. The added rigidity supplied by braces 21 and 22 helps maintain the sealing assembly 3 in a preferred alignment with the face of the wearer to ensure a proper and complete seal. Without the braces, the mask body 2 would tend to expand outward under the pressure of the pressurized air pumped therein, increasing the risk that the seal between the wearer's face and the sealing assembly 3 will be broken. Any break in the seal will result in uncomfortable leaks which tend to tickle the wearer or create annoying noises.

Providing receivers for the securement strap fasteners 20 on the rigid braces 21 and 22 also reduces the forces acting on the flexible mask body 2 to help the mask body 2 retain its shape. Mounting the strap fasteners directly to the flexible mask body 2 would result in the tensioning forces exerted through the strap fastener to be concentrated to that portion of the mask where the strap fasteners are connected. By connecting the strap fasteners 20 to the rigid braces 21 and 22, the forces exerted by the strap fasteners can be more evenly distributed across the mask body 2.

It is to be understood that while certain forms of the present invention have been illustrated and described herein, it is not to be limited to the specific forms or arrangement of parts described and shown. For example, it is to be understood that with respect to the strap fasteners 20, the keyhole openings could be formed in each fastener base 78 and the mating posts 79 could be formed on and project outward from the rigid braces 21 and 22. It is foreseen that the mask 1 could be utilized without the braces 21 and 22. The location and positioning of the ribs 44 could be varied or the ribs 44 could be eliminated. The relative dimension and size of any of the components could be varied including the size of the inner and outer sealing flanges 37 and 38.

As used in the claims, identification of an element with an indefinite article "a" or "an" or the phrase "at least one" is intended to cover any device assembly including one or more of the elements at issue. Similarly, references to first and second elements is not intended to limit the claims to such assemblies including only two of the elements, but rather is intended to cover two or more of the elements at issue. Only where limiting language such as "a single" or "only one" with reference to an element, is the language intended to be limited to one of the elements specified, or any other similarly limited number of elements.

Having thus described the invention, what is claimed as new and desired to be secured by Letters Patent is as follows:

1. A respiratory mask comprising:
   a mask body defining a mask chamber for receiving the nose and mouth of the wearer;
   a resilient cushion connected to and extending from said mask body; said cushion including a first arcuate section curving from a periphery of said mask body inward toward a center of said mask chamber and a second arcuate section curving from and in an opposite direction relative to said first arcuate section and away from said mask chamber to form an s-shaped spring wherein said second arcuate section is compressible toward said first arcuate section;
   an inwardly projecting sealing flange connected to and extending inward relative to a distal end of said cushion and adapted to engage a face of the wearer inward from said distal end of said cushion.

2. The respiratory mask as in claim 1 further comprising:
   an outwardly projecting sealing flange extending outward relative to a distal end of said cushion and adapted to engage a face of the wearer outward from said distal end of said second arc.

3. The respiratory mask as in claim 2 further comprising:
   a plurality of flexible ribs formed in said second arc and resisting compression of said second arc.

4. The respiratory mask as in claim 3 wherein said mask body, said cushion, said inwardly and outwardly projecting sealing flanges and said flexible ribs are integrally formed from silicone.

5. The respiratory mask as in claim 2 wherein said inwardly and outwardly projecting sealing flanges cooperatively form a concave sealing flange assembly opening toward a face of a wearer of the mask.

6. The respiratory mask as in claim 1 wherein said cushion further includes a third arcuate section curving in an opposite direction from said second arcuate section.

7. The respiratory mask as in claim 1 wherein said mask body is cup shaped and formed from a relatively flexible material and said mask further includes a relatively rigid brace formed separate from and mounted on said mask body in overlapping relationship therewith and extending across a portion of said mask body adapted to be positioned over the nose of a wearer.

8. The respiratory mask as in claim 7 in combination with a headgear assembly having straps for holding the respiratory mask against the face of a wearer wherein at least one of said straps is removably connectable to said brace.

9. The respiratory mask as in claim 1 wherein said mask body is cup shaped and formed from a relatively flexible material and said mask further includes an upper brace formed separate from and mounted to said mask body in overlapping relationship therewith and extending across a portion of said mask body adapted to be positioned over the nose of a wearer and a lower brace formed separate from and mounted to said mask body in overlapping relationship therewith and extending across a portion of said mask body adapted to be positioned over the chin of a wearer.

10. The respiratory mask as in claim 9 in combination with a headgear assembly having straps for holding the respiratory mask against the face of a wearer wherein at least one of said straps is connectable to said upper brace.

11. The respiratory mask as in claim 1 wherein said resilient cushion reduces in thickness from said periphery of said mask body to a distal end thereof.

12. The respiratory mask as in claim 1 wherein said second arcuate section is shorter in radius than said first arcuate section.

* * * * *